US012711008B2

(12) United States Patent
Hanauer et al.

(10) Patent No.: US 12,711,008 B2
(45) Date of Patent: Aug. 18, 2026

(54) ANOMALY DETECTION AND PERFORMANCE ASSESSMENT USING A PROVIDER PERFORMANCE INDEX

(71) Applicant: MedeAnalytics, Inc., Richardson, TX (US)

(72) Inventors: Matthew Hanauer, Durham, NC (US); Oxana Matveyuk, San Francisco, CA (US); Petro Krasniatov, Poznan (PL); Robert Corrigan, Riverside, IL (US); David Wolf, Atlanta, GA (US); Melissa Linder, Camdenton, MI (US); David Schweppe, Walnut Creek, CA (US); Madeline Hasegawa, Boise, ID (US)

(73) Assignee: MedeAnalytics, Inc., Richardson, TX (US)

( * ) Notice: Subject to any disclaimer, the term of this patent is extended or adjusted under 35 U.S.C. 154(b) by 50 days.

(21) Appl. No.: 18/821,242

(22) Filed: Aug. 30, 2024

(65) Prior Publication Data

US 2026/0064516 A1 Mar. 5, 2026

(51) Int. Cl.

| | |
|---|---|
| ***G16H 10/00*** | (2018.01) |
| ***G06F 11/07*** | (2006.01) |
| ***G06N 20/00*** | (2019.01) |
| ***G16H 50/30*** | (2018.01) |
| ***G16H 50/70*** | (2018.01) |
| *G16H 10/60* | (2018.01) |

(52) U.S. Cl.
CPC ........ *G06F 11/079* (2013.01); *G06F 11/0709* (2013.01); *G06N 20/00* (2019.01); *G16H 50/30* (2018.01); *G16H 50/70* (2018.01); *G16H 10/00* (2018.01); *G16H 10/60* (2018.01)

(58) Field of Classification Search
CPC ........ G16H 50/30; G16H 50/70; G16H 50/20; G06F 11/079
See application file for complete search history.

(56) References Cited

U.S. PATENT DOCUMENTS

| | | | |
|---|---|---|---|
| 8,583,450 B2 | 11/2013 | Baker et al. | |
| 10,354,755 B2 | 7/2019 | Norris et al. | |
| 10,643,749 B1 * | 5/2020 | Warner | G06N 5/041 |
| 11,521,148 B2 | 12/2022 | Wilkerson et al. | |
| 11,783,265 B2 | 10/2023 | Wilkerson et al. | |
| 11,869,656 B1 | 1/2024 | Stein | |
| 11,869,675 B2 | 1/2024 | Frey et al. | |

(Continued)

*Primary Examiner* — Jonathan D Gibson
(74) *Attorney, Agent, or Firm* — Sterne, Kessler, Goldstein & Fox P.L.L.C.

(57) ABSTRACT

Disclosed herein are system, method, and computer program product embodiments for creating and utilizing machine learning models to generate a provider performance index. In some embodiments, a first and second target may be selected. The first and second targets may respectfully include target values. First and second adjusted target values may be determined by combining the first and second target values with first and second external weights. The external weights may be generated by respective first and second machine learning models. The machine learning models may correspond to the respective targets. First and second error values may be determined based on differences between respective target and adjusted target values. The error values may be normalized and combined to generate an index value.

20 Claims, 12 Drawing Sheets

700

(56) References Cited

U.S. PATENT DOCUMENTS

| | | | | |
|---|---|---|---|---|
| 12,033,746 | B2 * | 7/2024 | Masson | G16H 40/20 |
| 12,367,953 | B1 * | 7/2025 | Babu | G16H 50/70 |
| 12,475,982 | B1 * | 11/2025 | Mouléne | G16H 20/00 |
| 2012/0078651 | A1 | 3/2012 | Henderson et al. | |
| 2012/0179487 | A1 | 7/2012 | Tawil | |
| 2014/0081652 | A1 * | 3/2014 | Klindworth | G06Q 10/0635 705/2 |
| 2016/0314255 | A1 * | 10/2016 | Cook | G06F 16/906 |
| 2018/0330825 | A1 * | 11/2018 | Sharifi | G16H 50/30 |
| 2019/0108898 | A1 * | 4/2019 | Gulati | G16H 10/60 |
| 2019/0347700 | A1 | 11/2019 | Shariff et al. | |
| 2020/0294642 | A1 * | 9/2020 | Bostic | G16H 50/20 |
| 2021/0241204 | A1 | 8/2021 | Stein | |
| 2023/0145258 | A1 * | 5/2023 | Jessen | G16H 50/20 706/12 |
| 2024/0257926 | A1 * | 8/2024 | Langel | G16H 10/20 |
| 2024/0370902 | A1 * | 11/2024 | Miglani | G16H 40/00 |
| 2025/0087342 | A1 * | 3/2025 | Khosla | G16H 40/20 |
| 2025/0339103 | A1 * | 11/2025 | Ptaszek | G06N 3/045 |

* cited by examiner

10th Percentile

| Provider | Provider Index | Preventative Screenings | Immunizations | Member Retention |
|---|---|---|---|---|
| Provider C | .7 | .2 | .4 | .3 |

90th Percentile

| Provider | Provider Index | Preventative Screenings | Immunizations | Member Retention |
|---|---|---|---|---|
| Provider A | 1.5 | 1.6 | 1.4 | 1.5 |

800

ANOMALY DETECTION AND PERFORMANCE ASSESSMENT USING A PROVIDER PERFORMANCE INDEX

BRIEF SUMMARY

Disclosed herein are system, apparatus, device, method and/or computer program product embodiments, and/or combinations and sub-combinations thereof, for creating and utilizing machine learning models to generate a provider performance index, and using the generated index to detect anomalies and assess performance. Some embodiments relate to a method comprising: selecting a first target, where the first target includes a first target value. The method further comprises determining a first adjusted target value by combining the first target value with a first external weight generated by a first machine learning model. The first external weight may correspond to the first target, and to an impact of one or more features associated with the first target. The first machine learning model may correspond to the first target. The method further comprises determining a first error value based on the first target value and the first adjusted target value. Next, the method normalizes the first error value via a statistical measure. The method then selects a second target, where the second target includes a second target value. The method then determines a second adjusted target value by combining the second target value with a second external weight generated by a second machine learning model. The second external weight may correspond to the second target, and to an impact of one or more features associated with the second target. The second machine learning model may correspond to the second target. The method may then determine a second error based on the second target value and the second adjusted target value, and normalize the second error value error via the statistical measure. The method may then generate an index value based on the first normalized error and second normalized error.

Some embodiments relate to a system comprising: a memory; and at least one processor coupled to the memory and configured to: select a first target, where the first target includes a first target value. The at least one processor may be further configured to determine a first adjusted target value by combining the first target value with a first external weight generated by a first machine learning model. The first external weight may correspond to the first target, and to an impact of one or more features associated with the first target. The first machine learning model may correspond to the first target. The at least one processor may be further configured to determine a first error value based on the first target value and the first adjusted target value and normalize the first error value via a statistical measure. The at least one processor may be further configured to select a second target, where the second target includes a second target value. The at least one processor may be further configured to determine a second adjusted target value by combining the second target value with a second external weight generated by a second machine learning model. The second external weight may correspond to the second target, and to an impact of the one or more features associated with the second target. The second machine learning model may correspond to the second target. The at least one processor may be further configured to determine a second error based on the second target value and the second adjusted target value and normalize the second error value error via the statistical measure. The at least one processor may be further configured to generate an index value based on the first normalized error and second normalized error.

Some embodiments relate to a non-transitory computer-readable device having instructions stored thereon. When the instructions are executed by at least one computing device, the instructions cause the at least one computing device to perform operations comprising: selecting a first target, where the first target includes a first target value. The operations further comprise determining a first adjusted target value by combining the first target value with a first external weight generated by a first machine learning model. The first external weight may correspond to the first target, and to an impact of the one or more features associated with the first target. The first machine learning model may correspond to the first target. The operations further comprise determining a first error value based on the first target value and the first adjusted target value. Next, the operations normalize the first error value via a statistical measure. The operations then select a second target, where the second target includes a second target value. The operations then determine a second adjusted target value by combining the second target value with a second external weight generated by a second machine learning model. The second external weight may correspond to the second target, and to an impact of the one or more features associated with the second target. The second machine learning model may correspond to the second target. The operations may then determine a second error based on the second target value and the second adjusted target value, and normalize the second error value error via the statistical measure. The operations may then generate an index value based on the first normalized error and second normalized error.

BRIEF DESCRIPTION OF THE DRAWINGS

The accompanying drawings are incorporated herein and form a part of the specification.

In the drawings, like reference numbers generally indicate identical or similar elements. Additionally, generally, the left-most digit(s) of a reference number identifies the drawing in which the reference number first appears.

DETAILED DESCRIPTION

Figure 1:
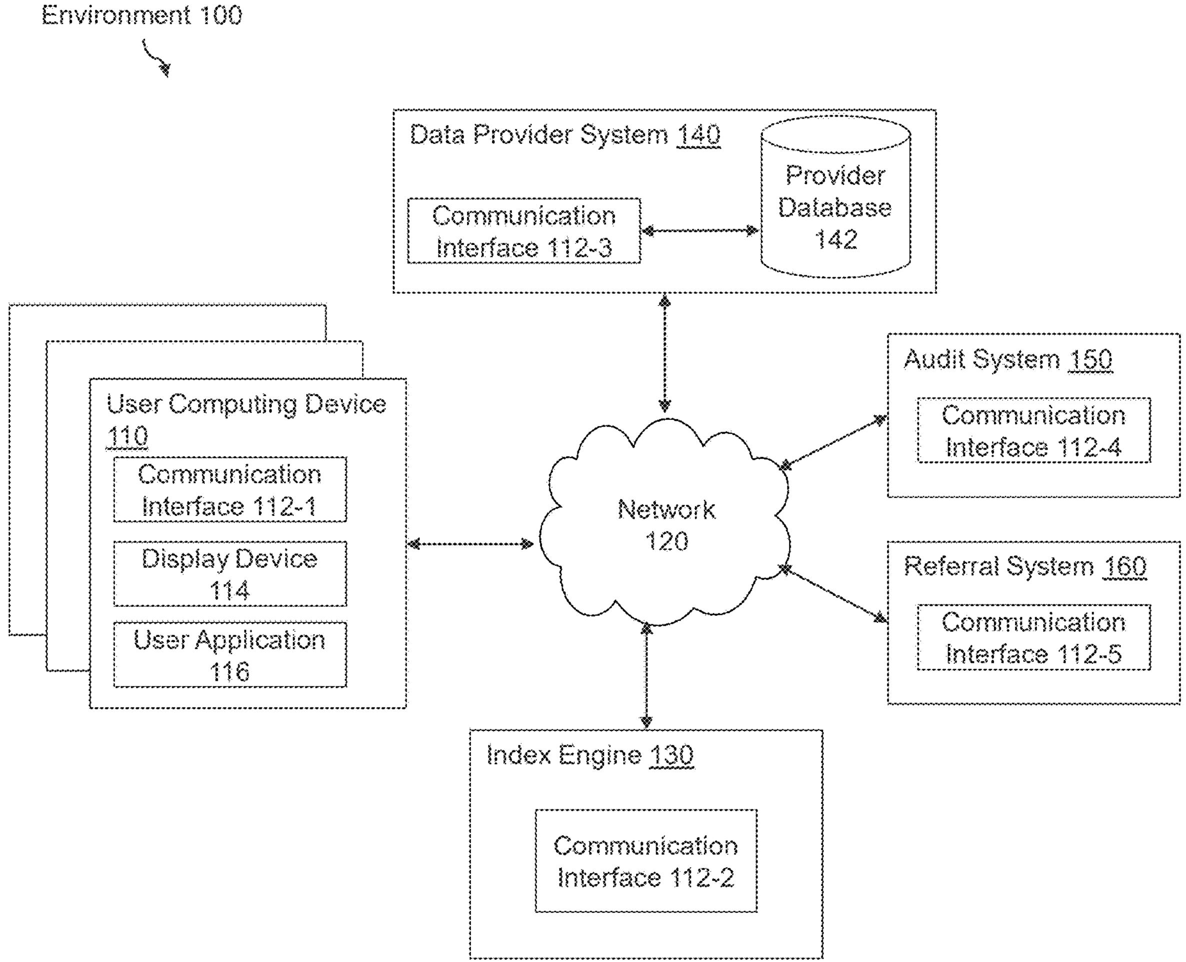
FIG. 1 depicts exemplary environment for generating a provider performance index, according to some embodiments.

Provided herein are system, apparatus, device, method and/or computer program product embodiments, and/or combinations and sub-combinations thereof, for creating and utilizing machine learning models to generate a provider performance index.

Many industries benefit from the ability to track and compare performance of practitioners. This is especially true in healthcare, where the quality of care and the subsequent effects on patient outcomes can vary widely. Two surgeons, facing similarly situated patients, may each apply different surgical techniques, generating two different outcomes. For example, one patient may be cured using the first technique, while the other technique may fail, or lead to further, potentially life-threatening complications. Thus, there is a clear need to be able to accurately, and reliably compare providers. This is critical, not only to stop and prevent faulty, ineffective, or otherwise defective treatment methods, but also to refine, improve, and otherwise encourage effective treatment methods. This need is further heightened given external factors (e.g., features). For example, in addition to the two surgeons applying different surgical techniques, they may also treat different patient populations. As a result, discrepancies in patient outcomes may be attributable to a combination of the techniques applied, and the impact of the features associated with patient populations.

For example, the first surgeon may treat patients in a rural area, whereas the second surgeon may treat patients in an urban area. Although the surgeons may apply the same techniques, the fact that the patients come from different populations, may impact treatment outcomes. In order to identify both defective and effective treatment methods, there is a need to remove impact of features from provider treatment outcomes.

Current methods to generate a provider index have numerous shortfalls. First, many current systems rely on surveys or other subjective methodologies. For example, many provider systems (e.g., private practices, hospitals) may use survey data to determine provider effectiveness. Survey data may be ineffectual because it relies upon the respondent to provide, accurate information. Second, current systems lack the ability to capture provider data in real-time. As discussed above, provider decisions may have life-threatening effects. Therefore, the ability to make decisions regarding provider treatment methods in real-time may save lives. Additionally, surveys or other manual techniques fail to capture all data. Third, current systems may lack the ability to compare providers given various external factors. For example, current systems may be unable to compare providers across geographic regions, specialties, and patient populations. Lastly, current systems often rely on human operators to gather and analyze provider data. However, given the amount of healthcare data available, it would be impractical for a human operator to sift through the data to generate an index, let alone provide real-time results. Thus, there is a need to generate improved provider indexes.

The index engine and associated methods described herein improve upon provider index generation by generating real-time provider index scores. The index engine may capture provider data in real-time, from various sources such as hospitals, urgent care facilities, private practices, etc. Once retrieved, the data may be validated. For example, the index engine may require certain fields, such as a provider identifier, provider type (e.g., doctor, nurse, physician assistant), and department/field (e.g., emergency medicine, pediatrics, internal medicine) to be present in the data.

The index engine may also determine whether targets, used to generate the index, are present in the received data. Targets may be categories of data used to construct an index. Targets may have corresponding values. Example targets may include an average patient length of stay or a provider's generic prescription dispensing rate. If the index engine is going to use a target such as generic prescription dispensing rate to generate an index, the index system may check whether the generic prescription dispensing rate target is present in each data item. In some embodiments, if a target is missing, the index engine may not include the item in the index calculation process. In some embodiments, the index engine may request updated data from the provider system.

The index engine may further perform one or more transformations on the data. For example, the index engine may convert the data into a standardized format by changing the unit of a target value or combining targets. The index engine may further create an encoded version of the data by transforming it into a numerical format. For example, the index engine may create a numerical vector, where each target value is placed at a predetermined index within the vector.

Once transformed, the index engine may apply one or more machine learning models to the data. Each target may have a corresponding model. The machine learning models may be trained to remove the impact of one or more features (e.g., external factors) for the given target. It may be beneficial to utilize different machine learning models for different targets because targets may have varying impacts on targets. For example, a feature such as average patient age may impact targets such as average opioid prescription rate and average length of stay, differently. Thus, in order to generate an accurate provider index it may be beneficial to utilize multiple machine learning models.

After inputting the target data into the corresponding models, the index engine may normalize each target and then aggregate the normalized target values. Normalizing targets may be beneficial to ensure that targets are on the same scale. For example, average patient age and average opioid prescription rate may have different units (e.g., number of years and mg/day). Therefore, normalizing the targets allows them to be compared more effectively. The index engine may then aggregate the normalized targets. For example, the index engine may compute the average of the normalized target scores to generate the index. The index engine may perform this step for each provider within the data set, in order to generate the provider index. Once generated, the index engine may perform one or more real-time actions. For example, the index engine may generate real-time alerts or notifications based upon the index scores.

The alerts may be based upon the index score itself, or based upon individual target scores. For example, an alert may be generated based on a target score corresponding to immunization rate that is below a predefined threshold.

Example targets may include, without limitation: (1) allowed per member per month (PMPM); (2) prevention and wellness; (3) Healthcare Effectiveness Data and Information Set (HEDIS) wellness visit; (4) HEDIS preventative screenings: (5) HEDIS immunizations; (6) HEDIS chronic care management; (7) HEDIS care coordination; (8) generic dispensing rate; (9) member retention; (10) average length of stay; (11) unplanned readmissions; and (12) denial rate.

Allowed PMPM may be the average of Allowed Charges covered by health benefit plan divided by total months patient is enrolled. Prevention and Wellness may be the average number of prevention and wellness related services a patient received during period including annual exams, immunizations, condition risk screenings, wellness education and coordination of care. HEDIS Wellness Visits may be the percentage of patients complying with National Committee for Quality Assurance (NCQA) evidence-based guidelines for adult, children and pregnancy wellness exams. HEDIS Preventive Screenings may be the percentage of patients complying with NCQA evidence-based guidelines for cancer screenings and other at-risk condition screenings. HEDIS Immunizations may be the percentage of patients complying with NCQA evidence-based guidelines for children and adolescents receiving recommended immunizations. HEDIS Chronic Care Management may be the percentage of patients with Diabetes, Hypertension, Asthma, COPD and Depression complying with NCQA evidence-based treatment guidelines. HEDIS Care Coordination may be the percentage of patients complying with NCQA evidence-based guidelines for transition of care and mental health follow-up care. Generic Dispensing Rate may be the percentage of pharmacy prescriptions filled with generic drugs. Member retention may be the net percentage of total patients joining or leaving. Average length of stay may be the average inpatient days per hospital admission. Unplanned readmission may be the percentage of total index admissions with an additional unplanned hospital admission within less than 30 days of prior index admission. Denial Rate may be the percentage of total medical claims submitted that were partially or fully denied for payment by health plan.

Various embodiments are described using these example features for purposes of illustration.

FIG. 1 depicts exemplary environment 100 for generating a provider index, according to some embodiments. Environment 100 may include user computing device 110, network 120, index engine 130, data provider system 140, audit system 150, and referral system 160.

User computing device 110 may be any entity attempting to communicate with index engine 130. Although a single user computing device 110 is depicted, environment 100 may include multiple user computing devices 110. User computing device 110 may be a computer system such as computer system 900 described with reference to FIG. 9. User computing device 110 may be a client system such as a desktop workstation, laptop or notebook computer, netbook, tablet, smart phone, and/or other computing device that may be using an enterprise computing system.

User computing device 110 includes communication interface 112-1, display device 114, and user application 116. Communication interface 112-1 may be configured to communicate with index engine 130 via network 120. Communication interface 112-1 may comprise any suitable network interface capable of transmitting and receiving data, such as, for example a modem, an Ethernet card, a communications port, or the like. Communication interface 112-1 may be able to transmit data using any wireless transmission standard such as, for example, Wi-Fi, Bluetooth, cellular, or any other suitable wireless transmission. Display device 114 may be configured to display information at user computing device 110. Display device 114 may be configured to receive interactions. An interaction may be, for example, a button press, swipe, touch, click, etc. User application 116 may be an app installed on user computing device 110 that interacts with index engine 130. A user may access, view, and interact with user application 116 via display device 114.

Network 120 may be any type of computer or telecommunications network capable of communicating data, for example, a local area network, a wide-area network (e.g., the Internet), or any combination thereof. The network may include wired and/or wireless segments. Network 120 may include one or more channels. For example, network 120 may include one or more virtual private network (VPN) connections. This may be beneficial to provide security for traffic sent over network 120. For example, data provider system 140 may use a VPN at network 120 to transmit data to index engine 130. Additionally, index engine 130 may request and receive data from data provider system 140 via a VPN at network 120.

Index engine 130 may be implemented using one or more servers and/or databases. In some embodiments, index engine 130 may be implemented using a computing device such as a desktop workstation, laptop or notebook computer, netbook, tablet, smart phone, and/or other computing device. In some embodiments, index engine 130 may be implemented as an application in an enterprise computing system and/or a cloud-computing system. In some embodiments, index engine 130 may be a computer system such as computer system 900 described with reference to FIG. 9. Index engine 130 may include communication interface 112-2 to communicate with entities on network 120. Communication interface 112-2 may be configured to communicate with index engine 130 via network 120. Communication interface 112-2 may comprise any suitable network interface capable of transmitting and receiving data, such as, for example a modem, an Ethernet card, a communications port, or the like. Communication interface 112-2 may be able to transmit data using any wireless transmission standard such as, for example, Wi-Fi, Bluetooth, cellular, or any other suitable wireless transmission.

Index engine 130 may be configured to access data from data provider system 140 and generate a provider index. As will be discussed further below, data provider system 140 may be a hospital, private practice, urgent care facility, or any other entity with access to provider data. Data provider system 140 may be configured to send data to index engine 130.

In some embodiments, index engine 130 may retrieve data from multiple data provider systems 140 in parallel. For example, index engine 130 may include one or more processors, where each of the one or more processors includes one or more executable threads. Each thread may be configured to continuously retrieve data from a data provider system 140. For example, a first thread may retrieve data from data provider system 140-1, while a second thread retrieves data from data provider system 140-2.

In some embodiments, index engine 130 may continuously retrieve data and update the index score based on the retrieved data. For example, index engine 130 may include an executable thread that continuously retrieves data and updates an index score, regardless of interaction from user computing device 110. This continuous retrieval may be beneficial further increase the speed at which user computing device 110 may receive an index from index engine 130. For example, user computing device 110 may connect to index engine 130 and view the most recent index scores for a selected set of providers. The ability to update and provide access to index scores in real time may be beneficial to detect and respond to both treatment trends and outcome trends in real-time.

Index engine 130 may perform various tasks to extract, reformat, and standardize data from data provider system 140. Index engine 130 may extract provider information from the data. For example, index engine 130 may identify a provider name, the provider's specialty, and the provider's institution (e.g., the hospital where the provider works) in a record (e.g., data) from data provider system 140. Index engine 130 may further extract external factor data. The external factor data may be linked to a provider and their patient population. External factor data may include, for example, average age, percentage male, percentage female, continuously enrolled months, concurrent risk score, prospective risk score, unique acute diagnoses, chronic condition diagnoses, inpatient claimants, and member count. In some embodiments, external factor data may be common amongst providers. For example, two providers within the same practice group (e.g., pediatrics) may have the same average patient age. In some embodiments, external factor data may be unique to a provider. In some embodiments, external factor data may be unique to a group of providers or a specialty.

Index engine 130 may further extract one or more targets from the received data. A target may be a category of data used to generate a provider index. An example target may be opioid prescription rate. A target may include a target value, corresponding to the target. For example, if the target is opioid prescription rate, the target value may be 100 mg/day. Index engine may group extracted target data for each provider. For example, index engine 130 may extract opioid prescription rates for Provider A and for Provider B. Index engine 130 may extract data by parsing the data for target keywords, phrases, tags, or other indicators.

In some embodiments, index engine 130 may convert the extracted target data into a numerical format. For example, index engine 130 may generate a numerical vector of the target values, where each target value is assigned to a vector index. Index engine 130 may generate a vector for each provider. In some embodiments, index engine 130 may combine the vectors to create a numerical matrix.

As discussed above, there may be various factors outside of a provider's control that impact a target and its associated target value. For example, prescription rates may be higher for an internal medicine physician whose average patient age is 60, versus another physician's whose average patient age is 25. Therefore, index engine 130 may determine an adjusted target value corresponding to the target, where the adjusted target value represents what the target value would be when the features (e.g., average patient age) are removed. Index engine 130 may determine the adjusted target value by combining the target value with an external weight. For example, the adjusted target value may be determined by adding, subtracting, or multiplying the target value with the external weight. The external weight may be generated by a machine learning model configured to learn the impact of the features (e.g., average patient age) on the target (e.g., prescription rate). In some embodiments, index engine 130 may utilize a minimum mean square error to determine the external weight for a given target.

In some embodiments, index engine 130 may include a machine learning model for each target. For example, index engine 130 may retrieve data including three targets such as prescription rate, percent immunizations, and average length of stay. In response, index engine 130 may leverage three machine learning models. In some embodiments, each machine learning model may be trained to generate an adjusted target value corresponding to the target, where the adjusted target value represents the target minus the impact of one or more features. In some embodiments, the machine learning model may be trained to generate an external weight that, when combined with the target value, produces the adjusted target value. As a result, the first external weight generated by the first machine learning model may corresponds to the first target. For example, the impact of average patient age (e.g., an external factor) may have a different impact on two different targets, such as opioid prescription rate and average length of stay, which would be represented by different external weights for the two targets. In some embodiments, the first external weight generated by the first machine learning model may be unique to the first target. Each feature may have a corresponding machine learning model. As a result, index engine 130 may rapidly detect the degree of impact external factors (e.g., features) have on various targets. Furthermore, the machine learning models may be updated much quicker, as opposed to utilizing a single, monolithic model. This also allows the machine learning models to be more precise since they are trained to remove the impact of external factors for a single target. Additionally, this method improves upon prior systems that rely on humans to collect survey data from providers. As stated above, this method is faulty because: (1) data collection is inconsistent; and (2) responses are subjective.

As discussed above, each machine learning model may be trained to generate a target value corresponding to the target, where the adjusted target value represents the target minus the impact of the features (e.g., external factors). The machine learning model may be trained by iterating over example data, generating a prediction, and updating the model based on the results.

In some embodiments, each example may include three components: (1) target data; (2) feature data; and (3) a label. The target data may include one or more data measures for a provider. Target data may include, but is not limited to: (1) per member per month (PMPM); (2) prevention and wellness; (3) Healthcare Effectiveness Data and Information Set (HEDIS) wellness visit; (4) HEDIS preventative screenings: (5) HEDIS immunizations; (6) HEDIS chronic care management; (7) HEDIS care coordination; (8) generic dispensing rate; (9) member retention; (10) average length of stay; (11) unplanned readmissions; and (12) denial rate. In some embodiments, the machine learning model may correspond to an external feature. As a result, the machine learning model may correspond to a single external feature that the provider is unable to control. External features may include, for example, average age, percentage male, percentage female, continuously enrolled months, concurrent risk score, prospective risk score, unique acute diagnoses, chronic condition diagnoses, inpatient claimants, and member count. In some embodiments, the machine learning model may correspond to multiple external features. For example, the machine learning model may be configured to predict an adjusted target value given multiple features. The label may be ground truth data including the adjusted feature value that the machine learning model is being trained to predict given the feature data.

The machine learning model may take as input the target and feature data, and generate a predicted adjusted target value. An error may be calculated based on a difference between the predicted adjusted target value and the actual adjusted target value (e.g., the label). The error may be used to update the machine learning model. The machine learning model may be represented by a set of weights and the error may be used to update the weights. For example, backpropagation may be used to update the weights given the calculated error value.

Index engine 130 may calculate an error value based on the difference between the predicted adjusted target value and the actual adjusted target value. For example, index engine 130 may retrieve a provider's average daily opioid prescription rate (e.g., a target). Index engine 130 may further retrieve or access feature data corresponding to the provider. Index engine 130 may input the target data (e.g., average daily opioid prescription rate) and the feature data to a machine learning model to predict an adjusted target value given the feature data (e.g., external factor data). Index engine 130 may calculate an error value based on a difference between the target value (e.g., the actual value) and the adjusted target value (e.g., the target value minus the impact of one or more features). Index engine may then normalize the error value via a statistical measure. For example, index engine may calculate a z-score using the error value. Index engine 130 may determine an index score for the provider by calculating an average of the statistical measures (e.g., z-scores) for each target. Index engine 130 may generate an index score for each provider in the received data. Once the index scores are generated, index engine 130 may perform various tasks.

In some embodiments, index engine 130 may update a display showing the index scores. In some embodiments, index engine 130 may further display the differences between target values and adjusted target values. This may be beneficial to determine the impact that each target has on the overall index score. Additionally, index engine 130 may be configured to generate alerts or notifications based on the index. In some embodiments, index engine 130 may generate and send a notification each time a new index score is calculated. For example, user computing device 110 may subscribe to index engine 130 and request notifications each time an index is calculated. In some embodiments user application 116 at user computing device 110 may be used to interface between user computing device 110 and index engine 130. In response, index engine 130 may send a notification to user computing device 110, causing a notification to display on display device 114. In some embodiments, index engine 130 may generate notifications based on index score. For example, index engine 130 may generate notifications for providers at the bottom half, bottom third, or bottom quarter of an index distribution. In some embodiments, index engine 130 may generate notifications based on individual target values. For example, index engine 130 may generate a notification if a target value differs from the adjusted target value by more than a predefined threshold. For example, index engine 130 may generate a notification if the target value differs from the adjusted target value by more than 20%.

Data provider system 140 may be any entity capable of generating and/or storing data. For example, data provider system 140 may be a hospital, an internet service provider, or a financial institution. Data provider system 140 includes communication interface 112-3 and provider database 142. Data provider system 140 may communicate with index engine 130, via communication interface 112-3, over network 120. Data provider system 140 may be in communication with data store 140 via network 120. Although a single data provider system 140 is depicted, environment 100 may include multiple data provider systems 140. Data provider system 140 may include communication interface 112-3 to communicate with entities on network 120. Data provider system may include provider database 142. Provider database 142 may be a memory storage device configured to store provider data. For example, provider database 142 may include provider data such as the provider's name, specialty, and institution. Provider database 142 may include target data for each provider. Targets may include, but are not limited to: (1) allowed PMPM; (2) prevention and wellness; (3) HEDIS wellness visit; (4) HEDIS preventative screenings: (5) HEDIS immunizations; (6) HEDIS chronic care management; (7) HEDIS care coordination; (8) generic dispensing rate; (9) member retention; (10) average length of stay; (11) unplanned readmissions; and (12) denial rate. Provider database 142 may further include external factor data for each provider. External factor data may include: average age, percentage male, percentage female, continuously enrolled months, concurrent risk score, prospective risk score, unique acute diagnoses, chronic condition diagnoses, inpatient claimants, and member count.

Audit system 150 may be associated with an entity responsible for auditing providers. For example, auditors associated with audit system 150 may be tasked with auditing pediatricians employed by a hospital. Audit system 150 may include communication interface 112-4 to communicate with entities on network 120. For example, audit system 150 may request index scores from index engine 130. Audit system 150 may use the index scores to determine whether to audit a provider and/or group of providers represented in the index scores. For example, audit system 150 may trigger an audit for providers within the $10^{th}$ percentile, $15^{th}$ percentile, or $20^{th}$ percentile of the index score distribution. Similarly, audit system 150 may trigger an audit based on individual targets. For example, index engine 130 may calculate index scores for a provider using targets such as member immunization rate, average length of stay, and opioid prescription rate. As discussed above, index engine 130 may calculate an error value by calculating a difference between the target value and the predicted adjusted target value. In some embodiments, audit system 150 may trigger an audit when the error value exceeds a predefined threshold.

Referral system 160 may be associated with an entity configured to refer patients to providers. Referral system 160 may include communication interface 112-5 allowing referral system 160 to communicate with entities on network 120. Referral system 160 may receive target and feature data corresponding to a patient. For example, a patient may interact with user computing device 110 to send target and feature data to referral system 160. In some embodiments, referral system 160 may request patient data from a healthcare provider associated with data provider system 140 (e.g., a hospital). User computing device 110 may include additional information such as a location and a radius. Referral system 160 may query index engine 130 for index scores in response to the input from user computing device 110 and/or data provider system 140.

For example, referral system 160 may request index scores for providers within the radius of the location. Referral system 160 may then use a matching algorithm to pair the patient with a provider identified in the index scores. For example, referral system 160 may pair the patient with a provider based on the patient's target scores and the provider's adjusted target scores.

For example, the patient's target data may indicate that the patient prefers generic prescriptions over brand name prescriptions. Referral system 160 may use this information to pair the patient to a provider whose adjusted target score for generic prescription rate is high. For example, the paired provider may have an adjusted generic prescription rate score in the $90^{th}$ or $95^{th}$ percentile. Referral system 160 may suggest the identified provider to the patient. For example, referral system 160 may retrieve contact information associated with the provider from index engine 130 or data provider system 140. Referral system 160 may then forward the provider contact information to user computing device 110 associated with the patient.

Figure 2:
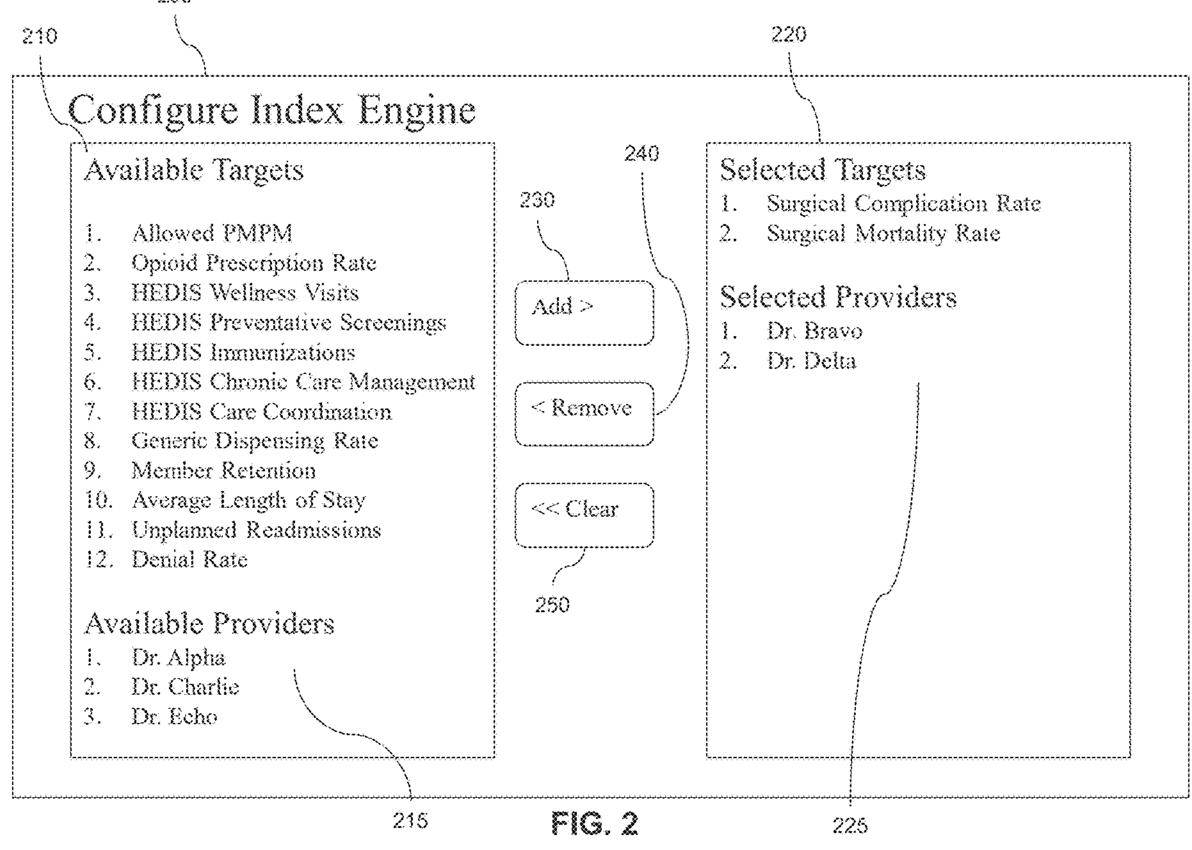
FIG. 2 depicts an exemplary interface for configuring an index engine, according to some embodiments.

FIG. 2 depicts an exemplary interface 200 for configuring index engine 130, according to some embodiments. Interface 200 includes available targets 210, available providers 215, selected target 220, selected providers 225, add 230, remove 240, and clear 250. Interface 200 may be displayed on user computing device 110 when a configuration option of user application 116 is accessed.

Available targets 210 may display targets that are available from data provider system 140. For example, when a user accesses interface 200 hosted by index engine 130, index engine 130 may establish a connection to data provider system 140 and query the targets that are available. In some embodiments, available targets 210 may be updated in real time based on the connection between index engine 130 and data provider system 140. For example, as data provider system 140 generates additional data, including additional targets, this may be detected by index engine 130 and updated on interface 200. Available targets 210 may not all be stored at index engine 130. For example, index engine 130 may only retrieve selected targets 220 out of those available at data provider system 140. In some embodiments, available targets 210 may display targets that are stored at data provider system 140 and index engine 130. For example, index engine 130 may have previously retrieved target data from data provider system 140 and stored it at local store 132.

Available providers 215 may display providers with associated data at data provider system 140. Similar to the features described above, when a user accesses interface 200 hosted by index engine 130, index engine 130 may establish a connection to data provider system 140 and query the providers for which data provider system 140 has data. In some embodiments, available providers 215 may be updated in real time based on the connection between index engine 130 and data provider system 140. For example, as data provider system 140 updates provider data, this may be detected by index engine 130 and updated on interface 200.

Selected targets 220 may list targets that have been selected to use for index calculation. Similarly, selected providers 225 may list providers that have been selected for the index calculation. Once selected, index engine 130 may retrieve target data corresponding to selected targets 220, for the providers identified in selected providers 225.

Add 230 may be used to add targets from available targets 210 to selected targets 220. For example, entries at available targets 210 may be highlighted and then added to selected targets 220 by clicking add 230. Add 230 may further be used to add providers from available providers 215 to selected providers 225. Remove 240 may remove selected targets 220 and/or selected providers 225. Once removed, index engine 130 may stop retrieving the target from data provider system 140 for selected providers 225. Similarly, if a provider is removed, index engine 130 may stop retrieving the provider's data from data provider system 140. Clear 250 may remove all selected targets 220 and all selected providers 225.

Figure 3A:
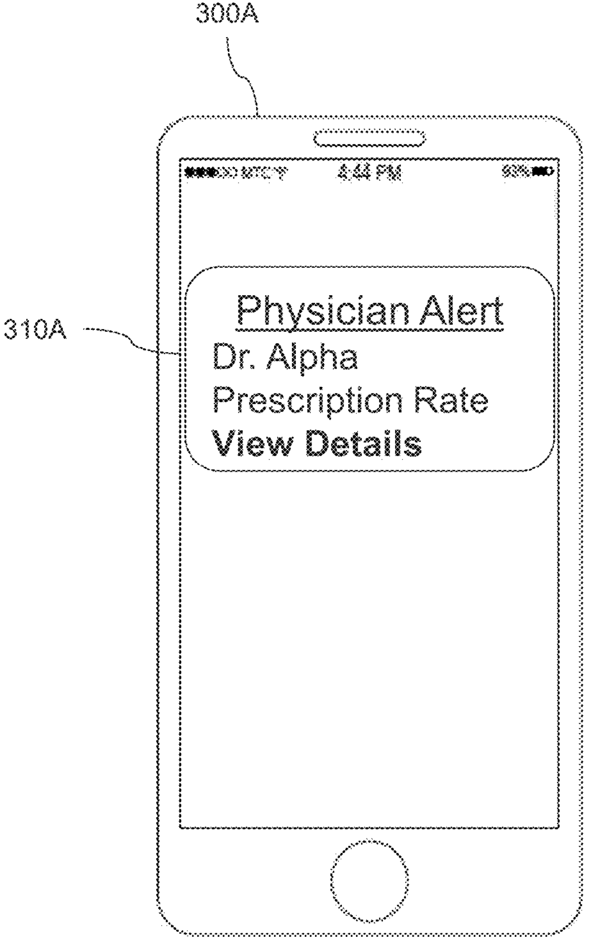
FIG. 3A depicts an exemplary interface for receiving and displaying an alert, according to some embodiments.
Figure 3B:
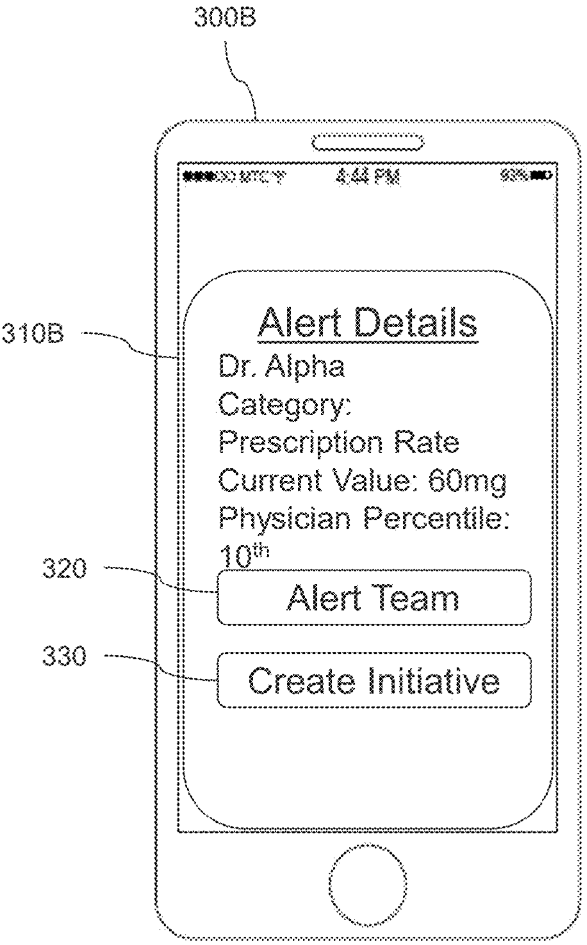
FIG. 3B depicts an exemplary interface for receiving and displaying an alert, according to some embodiments.

FIG. 3A depicts an exemplary interface 300A for receiving and displaying an alert, according to some embodiments. Interface 300A may display alert 310A on user computing device 110 when an alert is received. The alert may be received via network 120. The alert may be generated automatically by index engine 130 as a result of an index calculation. As discussed above, alerts may be generated when index scores are above or below certain threshold values. For example, an alert may be generated if an index, or a particular target index is within a percentile group (e.g., $10^{th}$ percentile). Such alerts provide real-time warnings regarding certain physician actions. For example, the amount of certain medications prescribed may be tracked in real time. This may be desirable to understand physician prescribing patterns, but also to identify potential illicit behavior by the physician. Additionally, it may be desirable to prevent medication from being overprescribed to patients. index engine FIG. 3B depicts an exemplary interface 300B for an alert, according to some embodiments. Interface 300B may display alert 310B on user computing device 110. Interface 300B may be shown when a user interacts with alert 310A. Alert 310B may display additional information regarding the received alert. For example, alert 310B may display the target to which the alert is linked, the current value of the target, and the percentile to which the physician is assigned based on the target value.

Interface 300B includes alert team 320 and restrict access 330. Alert team 320 may be configured to directly forward the alert to user computing devices 110 linked to the provider identified within the alert. For example, the provider may be part of a team, and each team member may receive the alert when alert team 320 is pressed. The alert may be forwarded via network 120. Alert team 320 may cause user computing devices 110 of the linked team members to display the alert. In some embodiments, the alert may cause user computing device 110 to vibrate and/or make a noise.

Interface 300B may further include create initiative 330. Create initiative 330 may be used to generate an initiative at index engine 130 linked to the target in the alert (e.g., prescription rate). Index engine 130 may use the initiative to automatically collect data associated with the target for tracking capabilities. For example, once the initiative is created, index engine 130 may continuously retrieve data including the target from data provider system 140.

Figure 4:
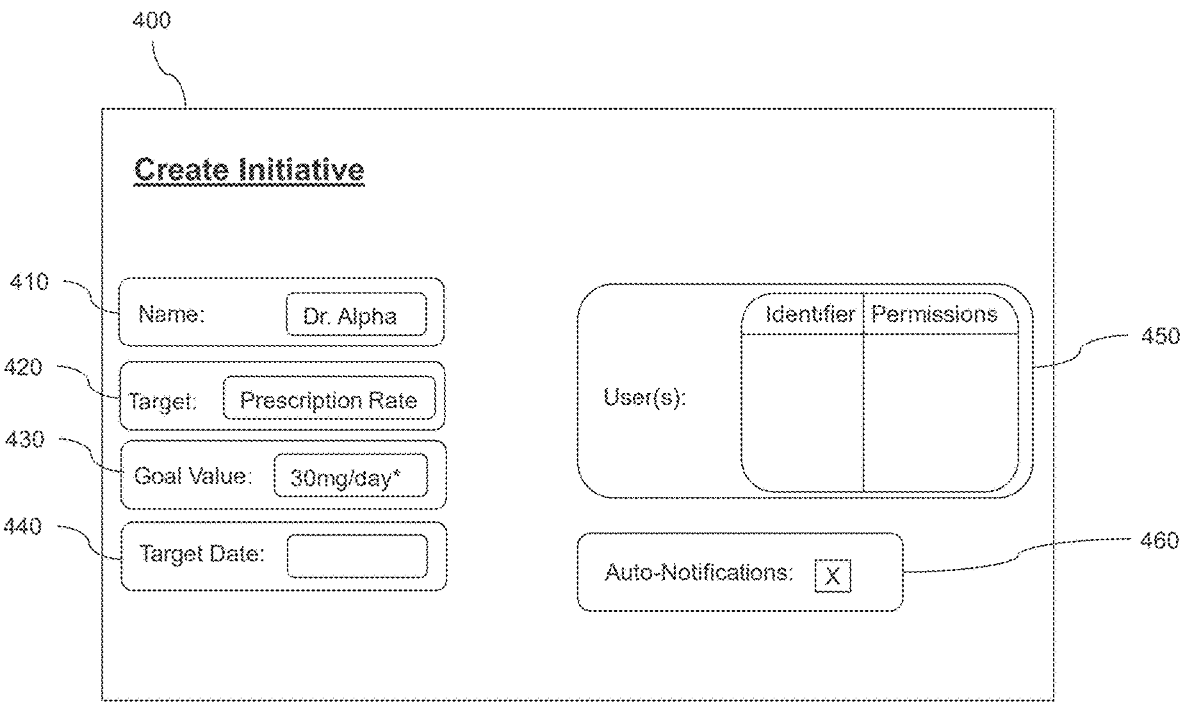
FIG. 4 depicts an exemplary interface for creating an initiative, according to some embodiments.

FIG. 4 depicts an exemplary interface 400 for creating an initiative, according to some embodiments. Interface 400 may be displayed on a computing device, such as user computing device 110, when accessing index engine 130. In some embodiments, interface 400 may be displayed as a result of a user at user computing device 110 selecting create initiative 540. An initiative may provide a way for index engine 130 to track providers. Initiatives may be linked to one or more targets. For example, an initiative may be tied to a single target such as opioid prescription rate. Additionally, an initiative may be associated with lowering costs. As a result, the initiative may be linked to one or more targets such as: (1) allowed PMPM; and (2) denial rate. Initiatives may be created by a user at user computing device 110 interacting with index engine 130. For example, user computing device 110 may create an initiative via user application 116. In some embodiments, initiatives may be created based on index engine's 130 index calculations.

For example, index engine 130 may be configured to automatically suggest an initiative to user computing device 110 based on index calculations. Index engine 130 may automatically suggest an initiative based on an index score, a target score, or a combination thereof. As discussed above, index engine 130 may calculate an error value by calculating a difference between the target value and the predicted adjusted target value. In some embodiments, index engine 130 may create an initiative when the error value exceeds a predefined threshold. In some embodiments, each target may have a unique predefined threshold. For example, daily opioid prescription rate may have a first predefined error threshold and average length of stay may have a second predefined error threshold. Index engine 130 may generate an initiative corresponding to the target. For example, if the error value of a provider's daily opioid prescription rate exceeds the predefined error threshold, the initiative may be targeted at reducing the error value. An initiative may have a termination condition at which point index engine 130 ceases automatically collecting and tracking target data associated with the initiative. In some embodiments, the termination condition may be reducing the error value such that it is less than or equal to the predefined error threshold. In some embodiments, the termination condition may be a length of time such as one week, one month, or one year. In some embodiments, the termination condition may include multiple conditions. For example, the initiative may terminate when either the error value is less than or equal to the predefined error threshold or after one month, whichever occurs first.

In some embodiments, index engine 130 may suggest an initiative based on an index score corresponding to a provider. For example, index engine 130 may suggest an initiative for all provider's within a certain percentile of the index score calculate (e.g., $10^{th}$ percentile, $20^{th}$ percentile, and/or $25^{th}$ percentile). The initiative may be configured to improve the target values used to calculate the index score. For example, if the index score was generated using targets such as allowed PMPM, average daily opioid prescription rate, and average surgical error rate, the initiative may also include those targets. As discussed above, an initiative may have a termination condition. Here, the termination condition may be tied to the index score, a duration of time, or any other measure. For example, the initiative may terminate once the provider's index score increases to a certain percentile (e.g., $50^{th}$ percentile).

In some embodiments, index engine 130 may automatically create the initiative. In some embodiments, index engine 130 may generate an initiative and send a prompt to user computing device 110 to approve the initiative. For example, index engine 130 may generate an initiative and send a notification to user computing device 110. A user at user computing device 110 may accept, deny, or edit the initiative. For example, the user may add or remove features from the initiative generated by index engine 130. Once created, index engine 130 may automatically and continuously retrieve data associated with an initiative. For example, index engine 130 may, for each target included within an initiative, continuously retrieve from data provider system 140 and use to recalculate an index score. Index engine 130 may stop retrieving data once a termination condition is reached. In some embodiments, index engine 130 may alert or notify a user associated with user computing device 110 when a termination condition is reached.

Interface 400 may include various fields, such as name 410, target 420, goal value 430, target date 440, users 450, and notifications 460. Various fields at interface 400 may be auto-populated as a result of an alert. For example, name 410, target 420, goal value 430 may be auto-populated from the alert. Fields such as name 410 and target 420 may be copied from the alert. In some embodiments, fields may be calculated. For instance, goal value 430 may be calculated based on the index that led to the alert. For example, goal value 430 may be the average value from the calculated index for the target. As another example, index engine 130 may have calculated an index score for one or more providers using data from data provider system 140. The index calculation may have included various targets such as allowed PMPM, average opioid prescription rate, and average length of stay. Index engine 130 may be configured to generate alerts for targets based on configurable percentiles. For example, index engine 130 may generate an alert relating to a target within the $10^{th}$ percentile of the index calculation. In the example illustrated in FIG. 4, index engine 130 may have generated an alert based on determining that Dr. Alpha's opioid prescription rate (e.g., the target) was within the $10^{th}$ percentile for that target.

In some embodiments, fields of interface 400 may be edited. For example, a user at user computing device 110 may update goal value 430 from the auto-populated value to another value. Target date 440 may be a date/time field target 420 should reach goal value 430. For example, user at user computing device 110 may indicate Dr. Alpha's opioid prescription rate should fall from 60 mg/day to 30 mg/day by Aug. 1, 2024.

As stated above, user computing device 110 may define an initiative, and index engine 130 may be configured to retrieve targets associated with the initiative. Name 410 may be a name to identify the initiative. For example, name 410 may be a name of the provider linked to the initiative. Target 420 may be a target (e.g., data category) that index engine 130 may retrieve from data provider system 140. For example, target 420 may be opioid prescription rate. Goal value 430 may be a goal corresponding to target 420. For example, target 420 may correspond to the value of material wasted during surgical procedures and goal value 430 may be $0. Target date 440 may be a date by which user computing device 110 wishes target 420 to reach goal value 430. Target date 440 may include a date and/or time.

Users 450 may correspond to other user computing devices 110 that may access the initiative created via interface 400. User computing device 110 may identify other user computing devices 110 by listing identifiers (e.g., email address, phone number, employee ID). User computing device 110 may set permissions associated with each identifier. Permissions may be read or write. For example, user computing device 110-1 assigned read permissions may view the initiatives but not edit it. Additionally, user computing device 110-2 assigned write permissions may view and edit the initiative.

As discussed above, permissions may be used by index engine 130 to determine what actions a user computing device 110 may perform on index engine 130. Once added within users 450, each user computing device 110 may receive an alert or notification with a link to access an interface hosted by index engine 130 to view the initiative. Notifications 460 may be a checkbox indicating whether the user computing devices 110 should receive auto-notifications associated with the defined initiative. In some embodiments, notifications may be generated when target 420 reaches a threshold value, such as goal value 430.

Figure 5:
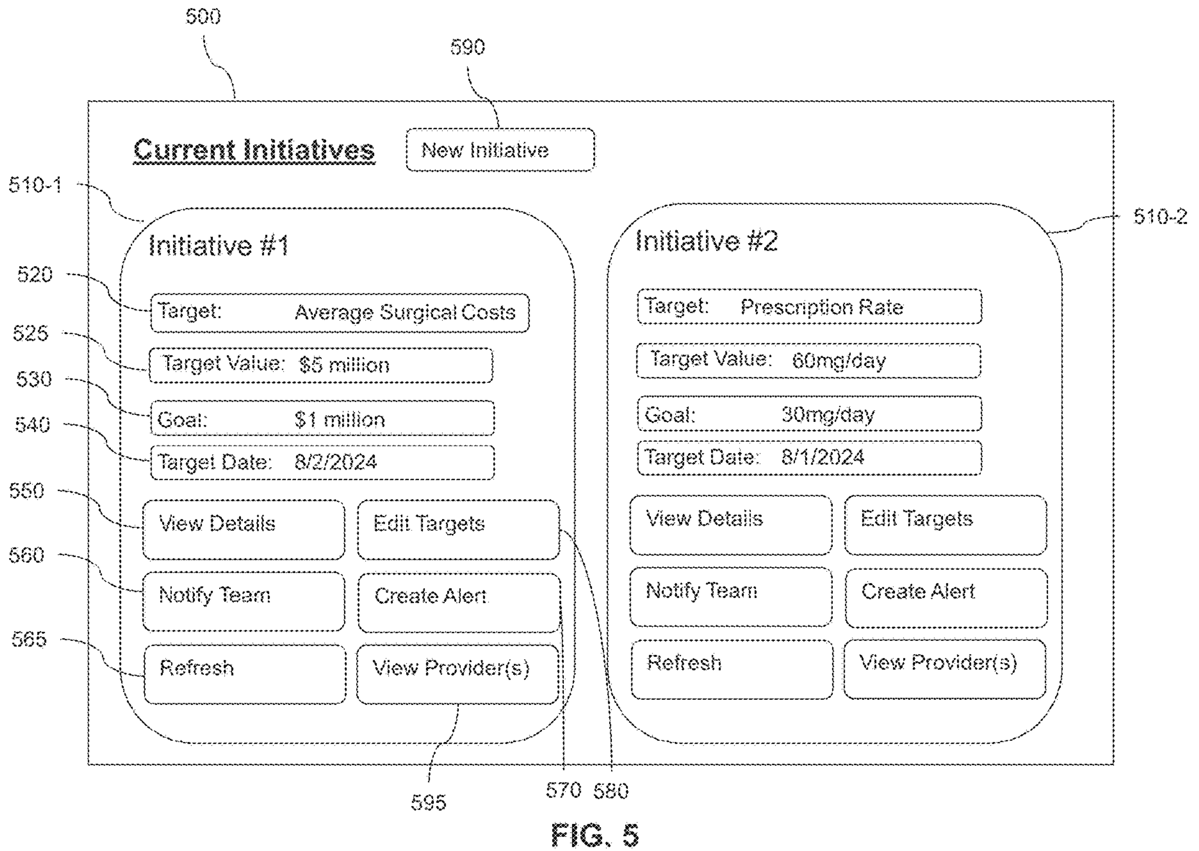
FIG. 5 depicts an exemplary interface for displaying initiatives, according to some embodiments.

FIG. 5 depicts an exemplary interface 500 for displaying initiatives, according to some embodiments. As described above, an initiative may be used to continuously track and display data from data provider system 140. User computing device 110 may access interface 500 when it connects to index engine index engine 130 via user application 116. Interface 500 includes initiative 510, target 520, target value 525, goal 530, target date 540, view details 550, notify team 560, refresh 565, create alert 570, edit feature 580, new initiative 590, and view providers 595. In some embodiments, user application 116 may be configured to automatically load interface 500 upon initiation of user application 116. Such operation enables the user operating user application 116 quick access to critical information relevant to the user, as discussed further below.

As depicted, interface 500 may display multiple initiatives, 510-1 and 510-2. Target 520 may be a target associated with initiative 510. Target 520 may be a data category that index engine index engine 130 retrieves from data provider system 140. For example, target 520 may be opioid prescription rate. Target value 525 may be the value corresponding to target 520. For example, target 520 may be opioid prescription rate and target value 525 may be 60 mg/day. Goal 530 may be a goal corresponding to target 520. For example, goal 530, corresponding to target 520, may be 30 mg/day. Target date 540 may be a date that user computing device 110 wishes target 520 to reach goal 530 by. Target date 540 may include a date and/or time. Initiative 510-1 and 510-2 may include multiple targets 520, target values 525, goals 530, and target dates 540.

View details 550 may enable user computing device 110 to view additional information regarding initiative 510. For example, initiative 510 may have multiple targets 520 associated with it and interface 500 may display a limited set. User computing device 110 may identify which targets 520 to display on interface 500. In some embodiments, index engine 130 may identify which targets 520 to display. In some embodiments, index engine 130 may configure interface 500 to display a target 520 with a target value 525 that changed the most over a certain time period. In some embodiments, index engine 130 may configure interface 500 to display a target 520 that is determined to have the most impact on initiative 510. In some embodiments, multiple targets may be displayed for each initiative. In some embodiments, the number of targets displayed may depend on available display real estate. In some embodiments, view details 550 may enable user computing device 110 to view each target (or a larger subset of targets) associated with the initiative stored at index engine 130.

Notify team 560 may be used to send a notification or alert to users associated with initiative 510. Create alert 570 may launch a new GUI screen to create an alert that will generate and send an alert or notification to user computing devices 110 associated with initiative 510. The alert may also be automatically generated based on an event occurring (e.g., a target passing a threshold, a target falling within a certain percentile). Edit targets 580 may be used to edit targets currently linked to initiative 510. For example, user computing device 110 may use edit targets 580 to launch a new GUI screen to remove current targets 520 and/or add new targets 520 to initiative 510. For example, initiative 510 may be associated with reducing surgical costs, and have target 520-1 associated with average surgery time. User computing device may click edit targets 580, generating a new GUI, to add target 520-2 associated with material lost per surgery. New initiative 590 may generate a new screen allowing user computing device 110 to create a new initiative 510.

View providers 595 may display a list of one or more providers associated with an initiative. Additionally, view providers 595 may be used to add or remove providers associated with the initiative.

Figure 6A:
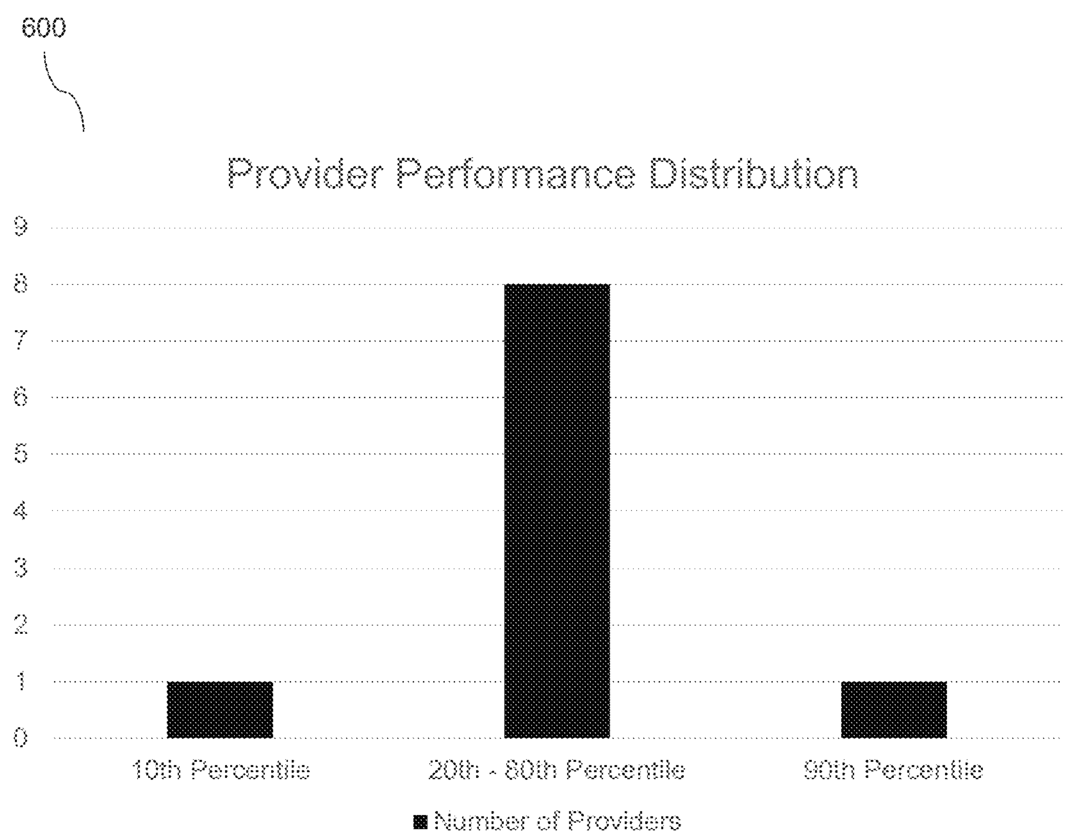
FIG. 6A depicts an exemplary interface for displaying a generated index, according to some embodiments.

FIG. 6A depicts an exemplary interface 600 for displaying a generated index, according to some embodiments. Index engine 130 may generate various interface 600 to display data regarding a generated index. For example, index engine 130 may generate a graph as depicted at interface 600, showing percentile breakdowns of providers included within the index calculation.

Figure 6B:
FIG. 6B depicts an exemplary interface for displaying a generated index, according to some embodiments.

FIG. 6B depicts an exemplary interface 600 for displaying a generated index, according to some embodiments. Index engine 130 may generate interface 600 to display a table including providers within each percentile. For example, index engine 130 may generate interface 600 and display providers within the $10^{th}$ and $90^{th}$ percentiles of the index. Interface 600 may display the index score for the provider. For Interface 600 may further include the targets included in the index calculation. For example, the index may have been calculated using preventative screenings, immunizations, and member retention.

Figure 6C:
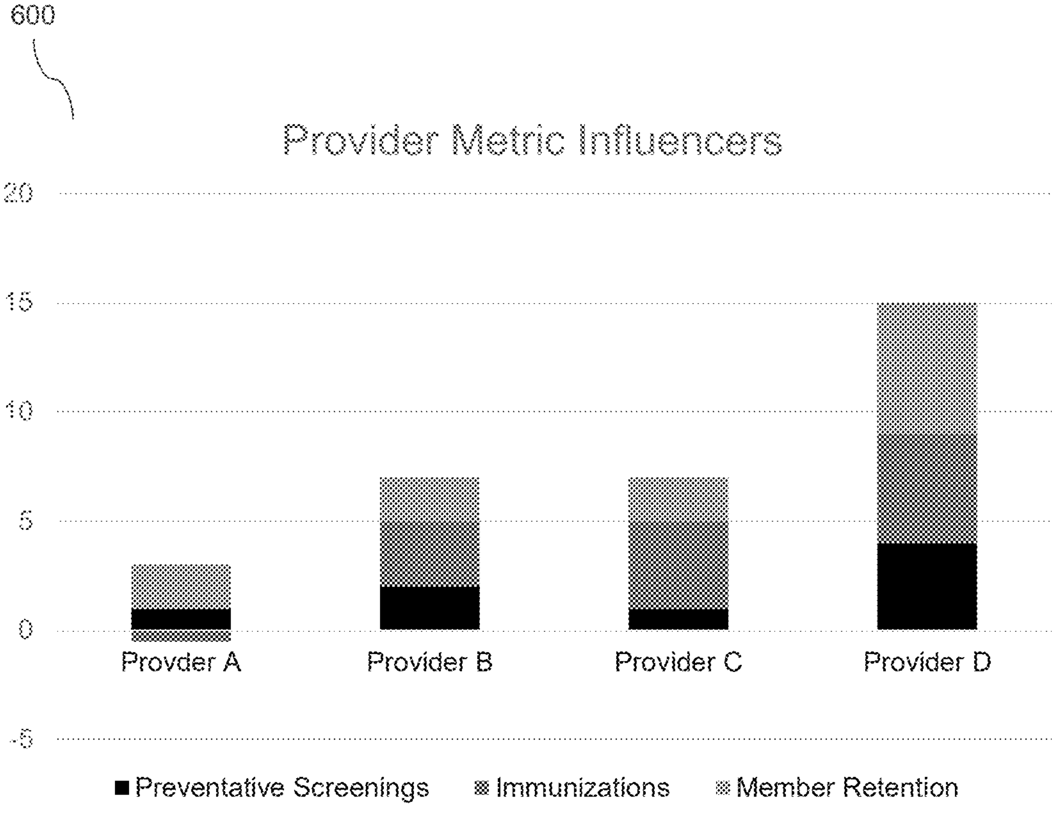
FIG. 6C depicts an exemplary interface for displaying a generated index, according to some embodiments.

FIG. 6C depicts an exemplary interface 600 for displaying a generated index, according to some embodiments. Index engine 130 may generate interface 600 showing a chart of providers included in the index calculation. The chart may include each provider included within the index calculation. The chart may further include each target used within the index calculation. For example, index engine 130 may have used targets such as preventative screenings, immunizations, and member retention to generate the index. Accordingly, these targets may be displayed within a chart as depicted at interface 600. The chart at interface 600 may depict the amount that each target contributed to the overall index score. As discussed above, the index may be an aggregate of each target included in the index calculation. In some embodiments, the index may be an average of each target. Here, index engine 130 may show relative or actual target values associated with each provider. This may be beneficial to understand overall index scores. For example, as illustrated in the chart at interface 600, although Provider B and C have similar overall index scores, Provider B has a more even distribution of scores across the included targets, whereas Provider C has a high score for immunizations but a low score for preventative screenings.

Figure 7:
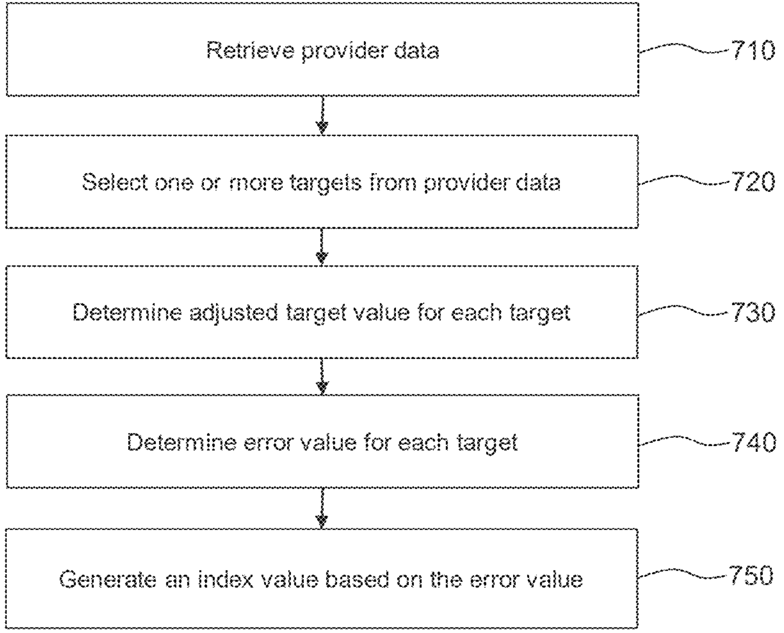
FIG. 7 is a flowchart illustrating an example process for generating a provider performance index, according to some embodiments.

FIG. 7 is a flowchart illustrating an example process 700 for generating a provider index, according to some embodiments. Method 700 shall be described with reference to FIG. 1, however, method 700 is not limited to that example embodiment.

In some embodiments, index engine 130 may utilize method 700 to generate a provider index using a data set. The following description will describe an embodiment of the execution of method 700 with respect to index engine 130. While method 700 is described with reference to index engine 130, method 700 may be executed on any computing device, such as, for example, the exemplary computer system described with reference to FIG. 9. Method 700 may be performed by processing logic that may comprise hardware (e.g., circuitry, dedicated logic, programmable logic, microcode, etc.), software (e.g., instructions executing on a processing device), or a combination thereof.

In some embodiments, one or more of the steps shown in FIG. 7 may be omitted, repeated, performed simultaneously, and/or performed in a different order than the order shown in FIG. 7. Accordingly, the scope of the invention should not be considered limited to the specific arrangement of steps shown in FIG. 7. The steps shown in FIG. 7 may be implemented as computer-readable instructions stored on computer-readable media, where, when the instructions are executed, cause a processor to perform the process of FIG. 7.

At 710, index engine 130 retrieves provider data. The provider data may be from data provider system 140. In some embodiments, data provider system 140 may automatically send (e.g., stream) data to index engine 130. In some embodiments, index engine 130 may request data from data provider system 140. In some embodiments, index engine 130 may retrieve provider data from multiple data provider systems 140. Index engine 130 may specify one or more providers from which to receive data. In some embodiments, index engine 130 may request specific data (e.g., targets) for each provider. In some embodiments, index engine 130 may request all data (e.g., all targets) for the given providers.

Index engine 130 may perform various operations on the data set. For example, index engine 130 may aggregate data by provider. As another example, index engine 130 may create and store one or more key-value pairings. A key may be a provider identifier such as a name or employee identifier. A value may be a collection of targets and corresponding target values.

At 720, index engine 130 selects one or more targets from the provider data. As discussed above, a target may be a category of data used to generate the index. Each target may include a corresponding value. For example, a target may be average opioid prescription rate and the corresponding target value may be 100 mg/day. In some embodiments, index engine 130 may select all targets present in the provider data. In some embodiments, index engine 130 may select a subset of targets present in the provider data. For example, user computing device 110 may configure index engine 130 to calculate a provider index using targets such as: (1) opioid prescription rate; (2) average length of stay; and (3) percentage of patients complying with immunization guidelines. User computing device 110 may configure index engine 130 via a web browser or mobile application, such as user application 116.

At 730, index engine 130 determines an adjusted target value for each target. Index engine 130 may determine the target value by combining the target value with an external weight. The external weight may be generated by applying a machine learning model to the target value. In some embodiments, the machine learning model may correspond to the target and be trained to remove the impact of one or more features (e.g., external factors) from the selected target. In some embodiments, the machine learning model may be unique to the target. A feature may be a data item that is outside the provider's control. For example, average patient age may be a feature.

In some embodiments, the external weight generated by the machine learning model may correspond to the target. In some embodiments, the external weight generated by the machine learning model may be unique to the target. External weights may reflect that certain targets are more or less impacted by features (e.g., external factors) than others. For example, a first target (e.g., average length of stay) may be more impacted by an external factor (e.g., social vulnerability index) than a second target (e.g., percentage of patients complying with wellness exam standards). The machine learning model may learn the correlation between targets (e.g., average prescription rate) and features (e.g., average patient age) via a training process. As described above, the machine learning model may be trained by taking as input target data and feature data. The machine learning model may then predict an external weight representing an amount to adjust the target data in order to remove the impact of the external factor data. In some embodiments, the machine learning model may predict an adjusted target value representing the target minus the impact of the feature data. An error may be calculated based on a difference between the predicted, adjusted target value and a label. The label may be the ground truth data given the target and feature data. In some embodiments, the machine learning model may directly predict the adjusted target value given the target value and feature data.

At 740, index engine 130 determines an error value for each target. In some embodiments, the error value may be determined by calculating a difference between the target value and the adjusted target value.

At 750, index engine 130 generates an index value based on the error value. In some embodiments, index engine 130 may generate the index value by taking an average of each error value. In some embodiments, index engine 130 may normalize each error value prior to generating the index. This normalization may be beneficial to ensure that the error values for each included target is on the same scale. For example, index engine 130 may determine a z-score for each error value.

In some embodiments, index engine 130 may weight each target prior to calculating the average. Weights may be used to determine the degree of impact the target should have in the calculated index. In some embodiments, user computing device 110 may configure index engine 130 with weights to use. For example, as opposed to determining the index by taking the average of each target value, index engine 130 may be configured to weight each target value. The weight may reflect the target's relative importance in the overall index score. For example, an index score may be calculated based on allowed PMPM, daily opioid prescription rate, an average length of stay. In some embodiments, the index may be computed based on an average of the computed error values for each target. In some embodiments, weights may be applied to the error values, prior to calculating an average. For example, allowed PMPM may be multiplied by a factor of 0.7, and daily opioid prescription rate may be multiplied by a factor of 1.1. In some embodiments, targets may have default weight values (e.g., 1.0). In some embodiments, user computing device 110 may configure target weights by interfacing with index engine 130.

Figure 8:
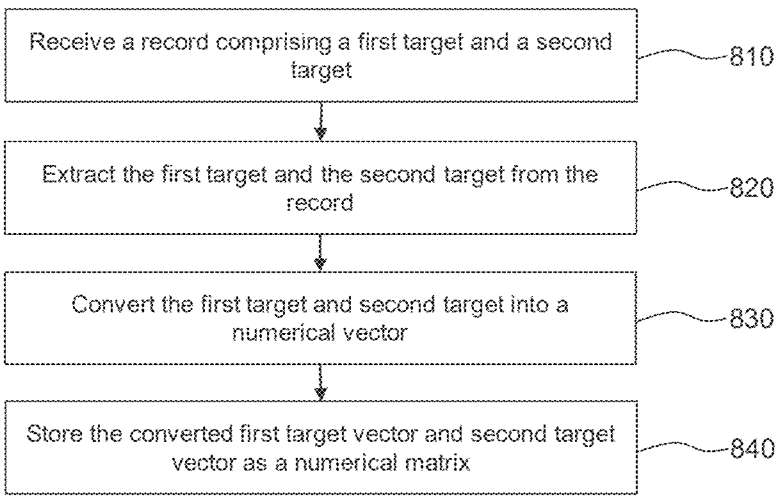
FIG. 8 is a flowchart illustrating an example process for extracting target data from a record, according to some embodiments.

In some embodiments, index engine 130 may publish or take other actions based on the index. For example, index engine 130 may send notifications to user computing devices 110 subscribed to receive the index value. index engine FIG. 8 is a flowchart illustrating an example process 800 for extracting target data from a record, according to some embodiments. Method 800 shall be described with reference to FIG. 1, however, method 800 is not limited to that example embodiment.

In some embodiments, index engine 130 may utilize method 800 to format data received from data provider system 140. The following description will describe an embodiment of the execution of method 800 with respect to index engine 130. While method 700 is described with reference to index engine 130, method 800 may be executed on any computing device, such as, for example, the exemplary computer system described with reference to FIG. 9. Method 800 may be performed by processing logic that may comprise hardware (e.g., circuitry, dedicated logic, programmable logic, microcode, etc.), software (e.g., instructions executing on a processing device), or a combination thereof.

In some embodiments, one or more of the steps shown in FIG. 8 may be omitted, repeated, performed simultaneously, and/or performed in a different order than the order shown in FIG. 8. Accordingly, the scope of the invention should not be considered limited to the specific arrangement of steps shown in FIG. 8. The steps shown in FIG. 8 may be implemented as computer-readable instructions stored on computer-readable media, where, when the instructions are executed, cause a processor to perform the process of FIG. 8.

At 810, index engine 130 receives a record comprising a first target and a second target. In some embodiments, the record may be from data provider system 140. In some embodiments, the record may correspond to a provider associated with data provider system 140. For example, data provider system 140 may be a hospital and the record may correspond to a physician employed by the hospital. In some embodiments, index engine 130 request the record from data provider system 140. In some embodiments, index engine 130 may request the record as part of an initiative. As discussed above, an initiative may be established to continuously track target data associated with a provider. The first target and second target may be any category of data corresponding to the provider. For example, the first target may be average length of stay and the second target may be daily opioid prescription rate.

At 820, index engine 130 extracts the first target and the second target from the record. Index engine 130 may include a list of targets to extract from a record. For example, index engine 130 may apply a parser to identify targets within the record. When a target is identified from the list of targets, index engine 130 may extract the target value. For example, the record may include an entry such as "Daily Opioid Prescription Rate: 1000 mg." Here, index engine 130 may detect that "Daily Opioid Prescription Rate" is included within the list of targets. As a result, index engine 130 may extract "1000 mg" and store it as a target value.

At 830, index engine 130 converts the first target and the second target into numerical vectors. Index engine 130 may generate one vector per target. Index engine 130 may use any embedding algorithm to generate the vectors such as BERT or word2vec. In some embodiments, index engine 130 may use an embedding algorithm such that the resulting numerical vector includes the semantic meaning of the target and target value. For example, values of numerical vectors corresponding to opioid prescription rate and generic prescription rate may be more similar than numerical vectors corresponding to opioid prescription rate and average length of stay.

At 840, index engine 130 stores the first target vector and the second target vector as a numerical matrix. For example, index engine 130 may combine the target vectors into a single matrix such that each row in the vector corresponds to a target. In some embodiments, index engine 130 may generate a label corresponding to the vector. In some embodiments, the label may be the name of the provider that the targets correspond to.

Once the matrix is constructed, index engine 130 may input the matrix into a machine learning model to determine adjusted target values for each target. For example, the machine learning model may be configured to predict target values for one or more targets, where the adjusted target value represents the target value minus the impact of one or more external factors (e.g., features). In some embodiments, the dimensions of the matrix may match the dimensions of the machine learning model. As a result, index engine 130 may calculate the dot product of the matrix and the machine learning model. The result may be a vector, where each value is an adjusted target value.

Although index engine 130 has been described in exemplary embodiments in the context of providers, the concepts described throughout the specification may be applied to other applications. For example, in some embodiments, a healthcare insurer may utilize index engine 130 to determine rates and/or benefits for members. For instance, the insurer may need to determine rates or benefits offered to two companies. The insurer may base the rates or benefits, in part, on the health of the company employees. For example, a company with healthier employees may receive cheaper rates and better benefits since they pose reduced risk to the insurer.

The insurer may obtain target data corresponding to the employees of each company. The target data may include the same data as described above with respect to providers. In some embodiments, target data may include data such as denial rates, emergency room visits, in-patient hospital visits, readmission rates, and generic prescription rates. The insurer may submit the target data for each company to index engine 130. As described above, index engine 130 may remove the impact of the features from the target data by applying one or more machine learning models. Similar to the targets, the features may be the same as those described above. In some embodiments, the features may include data such as age, gender, chronic conditions, and social determinants of health. Index engine 130 may then output a score for each company based on the targets minus the impact of the features.

The insurer may use the score to determine rates and/or benefits to offer the employees of each company. For example, a higher index score may correspond to healthier employees. As a result, the company with the higher index score may be offered better rates and benefits, as compared to the company with the lower index score.

As another example embodiment, index engine 130 may be used to assign providers to groups or subgroups. For example, providers in the $75^{th}$ percentile of a generated index may be assigned to a first provider group, and remaining providers may be assigned to a second provider group. The grouping may be used to determine treatment rates, accepted insurance policies, new patient criteria, referral policies, etc.

In some embodiments, the index may be used to group providers based on features corresponding to specific medical conditions or treatment methodologies. For example, index engine 130 may generate an index for a group of orthopedic surgeons treating a particular medical condition or performing a specific surgical procedure (e.g., rotator cuff repair, heart bypass surgery). The index may then be used to influence referral policies among provider networks, which may encourage members to obtain care from medical providers with a higher index score.

In some embodiments, the index created by index engine 130 may be used to determine revenue models. For example, a provider group may use the index generated by index engine 130 to allocate shared revenue or bonuses. For instance, index engine 130 may determine an index score for a group of providers by including a target such as revenue per member per month. The resulting index may then be used to allocate shared revenue or bonuses based on the index of revenue per member per month, minus the impact of included targets (e.g., external factors).

Figure 9:
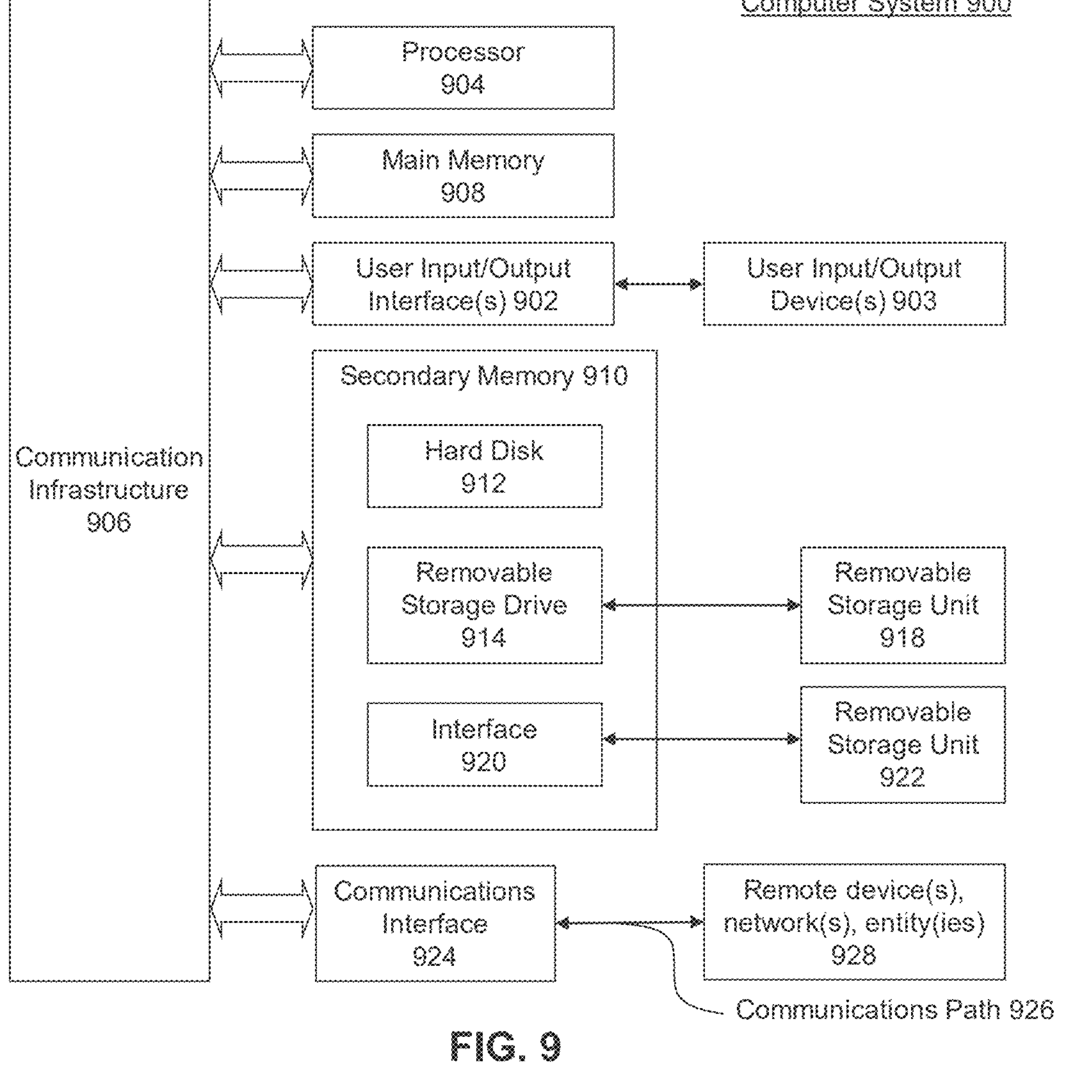
FIG. 9 depicts an example computer system useful for implementing various embodiments.

Various embodiments may be implemented, for example, using one or more well-known computer systems, such as computer system 900 shown in FIG. 9. One or more computer systems 900 may be used, for example, to implement any of the embodiments discussed herein, as well as combinations and sub-combinations thereof.

Computer system 900 may include one or more processors (also called central processing units, or CPUs), such as a processor 904. Processor 904 may be connected to a communication infrastructure or bus 906.

Computer system 900 may also include user input/output device(s) 903, such as monitors, keyboards, pointing devices, etc., which may communicate with communication infrastructure 906 through user input/output interface(s) 902.

One or more of processors 904 may be a graphics processing unit (GPU). In an embodiment, a GPU may be a processor that is a specialized electronic circuit designed to process mathematically intensive applications. The GPU may have a parallel structure that is efficient for parallel processing of large blocks of data, such as mathematically intensive data common to computer graphics applications, images, videos, etc.

Computer system 900 may also include a main or primary memory 908, such as random access memory (RAM). Main memory 908 may include one or more levels of cache. Main memory 908 may have stored therein control logic (e.g., computer software) and/or data.

Computer system 900 may also include one or more secondary storage devices or memory 910. Secondary memory 910 may include, for example, a hard disk drive 912 and/or a removable storage device or drive 914. Removable storage drive 914 may be a floppy disk drive, a magnetic tape drive, a compact disk drive, an optical storage device, tape backup device, and/or any other storage device/drive.

Removable storage drive 914 may interact with a removable storage unit 918. Removable storage unit 918 may include a computer usable or readable storage device having stored thereon computer software (control logic) and/or data. Removable storage unit 918 may be a floppy disk, magnetic tape, compact disk, DVD, optical storage disk, and/any other computer data storage device. Removable storage drive 914 may read from and/or write to removable storage unit 918.

Secondary memory 910 may include other means, devices, components, instrumentalities or other approaches for allowing computer programs and/or other instructions and/or data to be accessed by computer system 900. Such means, devices, components, instrumentalities or other approaches may include, for example, a removable storage unit 922 and an interface 920. Examples of the removable storage unit 922 and the interface 920 may include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computer system 900 may further include a communication or network interface 924. Communication interface 924 may enable computer system 900 to communicate and interact with any combination of external devices, external networks, external entities, etc. (individually and collectively referenced by reference number 928). For example, communication interface 924 may allow computer system 900 to communicate with external or remote devices 928 over communications path 926, which may be wired and/or wireless (or a combination thereof), and which may include any combination of LANs, WANs, the Internet, etc. Control logic and/or data may be transmitted to and from computer system 900 via communication path 926.

Computer system 900 may also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computer system 900 may be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computer system 900 may be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This includes, but is not limited to, computer system 900, main memory 908, secondary memory 910, and removable storage units 918 and 922, as well as tangible articles of manufacture embodying any combination of the foregoing. Such control logic, when executed by one or more data processing devices (such as computer system 900), may cause such data processing devices to operate as described herein.

Based on the teachings contained in this disclosure, it will be apparent to persons skilled in the relevant art(s) how to make and use embodiments of this disclosure using data processing devices, computer systems and/or computer architectures other than that shown in FIG. 9. In particular, embodiments can operate with software, hardware, and/or operating system implementations other than those described herein.

It is to be appreciated that the Detailed Description section, and not any other section, is intended to be used to interpret the claims. Other sections can set forth one or more but not all exemplary embodiments as contemplated by the inventor(s), and thus, are not intended to limit this disclosure or the appended claims in any way.

While this disclosure describes exemplary embodiments for exemplary fields and applications, it should be understood that the disclosure is not limited thereto. Other embodiments and modifications thereto are possible, and are within the scope and spirit of this disclosure. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments can perform functional blocks, steps, operations, methods, etc. using orderings different than those described herein.

References herein to "one embodiment," "an embodiment," "an example embodiment," or similar phrases, indicate that the embodiment described can include a particular feature, structure, or characteristic, but every embodiment can not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein. Additionally, some embodiments can be described using the expression "coupled" and "connected" along with their derivatives. These terms are not necessarily intended as synonyms for each other. For example, some embodiments can be described using the terms "connected" and/or "coupled" to indicate that two or more elements are in direct physical or electrical contact with each other. The term "coupled," however, can also mean that two or more elements are not in direct contact with each other, but yet still co-operate or interact with each other.

The breadth and scope of this disclosure should not be limited by any of the above-described exemplary embodiments, but should be defined only in accordance with the following claims and their equivalents.

What is claimed is:

1. A computer-implemented method, comprising:

selecting a first target, wherein the first target includes a first target value;

in real-time and based on selecting the first target:

retrieving a first dataset from a plurality of data sources, the first dataset comprising one or more features associated with the first target;

generating a first external weight by inputting the first target value and the one or more features associated with the first target into a first machine learning model corresponding to the first target, wherein the first machine learning model is configured to output an impact of the one or more features on the first target value;

generating a first adjusted target value by combining the first target value with the first external weight;

determining a first error value based on the first target value and the first adjusted target value; and normalizing the first error value via a statistical measure;

selecting a second target, wherein the second target includes a second target value;

in real-time and based on selecting the second target:

retrieving a second dataset from the plurality of data sources, the second dataset comprising one or more features associated with the second target;

generating a second external weight by inputting the second target value and the one or more features associated with the second target into a second machine learning model corresponding to the second target, wherein the second machine learning model is configured to output an impact of the one or more features on the second target value;

generating a second adjusted target value by combining the second target value with the second external weight;

determining a second error value based on the second target value and the second adjusted target value; and normalizing the second error value via the statistical measure; and in response to normalizing the second error value or normalizing the first error value:

generating an index value based on the first normalized error value and the second normalized error value; and transmitting, based on the index value being within a threshold percentile of a plurality of index values, an alert to one or more user computing devices.

2. The computer-implemented method of claim 1, wherein the index value is generated based on the average of the first normalized error value and the second normalized error value.

3. The computer-implemented method of claim 1, further comprising:

in response to generating the index value, automatically generating a message including the index value, the first target, and the second target; and transmitting the message via a network to the one or more user computing devices.

4. The computer-implemented method of claim 3, wherein the message comprises a link to access a graphical user interface (GUI) via the network, wherein the link is unique to the generated index value.

5. The computer-implemented method of claim 1, wherein the statistical measure is a z-score.

6. The computer-implemented method of claim 1, wherein the first and second machine learning models include one or more weights corresponding to average age, percentage male, percentage female, continuously enrolled months, concurrent risk score, prospective risk score, unique acute diagnoses, chronic condition diagnoses, inpatient claimants, or member count.

7. The computer-implemented method of claim 1, further comprising:

inputting, to the first machine learning model, target data associated with the first target and feature data associated with the one or more features;

generating, by the first machine learning model, an adjusted target value based on the target data and the feature data;

calculating an error by comparing the adjusted target value to an actual target value; and updating one or more weights of the first machine learning model using the calculated error.

8. The computer-implemented method of claim 1, further comprising:

receiving, at a server and from a data provider system, a record comprising the first target and the second target, wherein the record is in a non-standardized format;

extracting the first and second targets from the record;

converting the first and second targets into a numerical vector; and storing the converted first and second targets as a numerical matrix.

9. A system, comprising:

a memory; and at least one processor coupled to the memory and configured to:

select a first target, wherein the first target includes a first target value;

in real-time and based on selection of the first target:

retrieve a first dataset from a plurality of data sources, the first dataset comprising one or more features associated with the first target;

generate a first external weight by inputting the first target value and the one or more features associated with the first target into a first machine learning model corresponding to the first target, wherein the first machine learning model is configured to output an impact of the one or more features on the first target value;

generate a first adjusted target value by combining the first target value with the first external weight;

determine a first error value based on the first target value and the first adjusted target value; and normalize the first error value via a statistical measure;

select a second target, wherein the second target includes a second target value;

in real-time and based on selection of the second target:

retrieve a second dataset from the plurality of data sources, the second dataset comprising one or more features associated with the second target;

generate a second external weight by inputting the second target value and the one or more features associated with the second target into a second machine learning model corresponding to the second target, wherein the second machine learning model is configured to output an impact of the one or more features on the second target value;

generate a second adjusted target value by combining the second target value with the second external weight;

determine a second error value based on the second target value and the second adjusted target value; and normalize the second error value via the statistical measure; and in response to normalization of the second error value or normalization of the first error value:

generate an index value based on the first normalized error value and the second normalized error value; and transmit, based on the index value being within a threshold percentile of a plurality of index values, an alert to one or more user computing devices.

10. The system of claim 9, wherein the index value is generated based on the average of the first normalized error value and the second normalized error value.

11. The system of claim 9, wherein the at least one processor is further configured to:

in response to generating the index value, automatically generate a message including the index value, the first target, and the second target; and transmit the message via a network to the one or more user computing devices.

12. The system of claim 11, wherein the message comprises a link to access a graphical user interface (GUI) via the network, wherein the link is unique to the generated index value.

13. The system of claim 9, wherein the statistical measure is a z-score.

14. The system of claim 9, wherein the first and second machine learning models include one or more weights corresponding to average age, percentage male, percentage female, continuously enrolled months, concurrent risk score, prospective risk score, unique acute diagnoses, chronic condition diagnoses, inpatient claimants, or member count.

15. The system of claim 9, wherein the at least one processor is further configured to:

input, to the first machine learning model, target data associated with the first target and feature data associated with the one or more features;

generate, by the first machine learning model, an adjusted target value based on the target data and the feature data;

calculate an error by comparing the adjusted target value to an actual target value; and update one or more weights of the first machine learning model using the calculated error.

16. A non-transitory computer-readable device having instructions stored thereon that, when executed by at least one computing device, cause the at least one computing device to perform operations comprising:

selecting a first target, wherein the first target includes a first target value;

in real-time and based on selecting the first target:

retrieving a first dataset from a plurality of data sources, the first dataset comprising one or more features associated with the first target;

generating a first external weight by inputting the first target value and the one or more features associated with the first target into a first machine learning model corresponding to the first target, wherein the first machine learning model is configured to output an impact of the one or more features on the first target value;

generating a first adjusted target value by combining the first target value with the first external weight;

determining a first error value based on the first target value and the first adjusted target value; and normalizing the first error value via a statistical measure;

selecting a second target, wherein the second target includes a second target value;

in real-time and based on selecting the second target:

retrieving a second dataset from the plurality of data sources, the second dataset comprising one or more features associated with the second target;

generating a second external weight by inputting the second target value and the one or more features associated with the second target into a second machine learning model corresponding to the second target, wherein the second machine learning model is configured to output an impact of the one or more features on the second target value;

generating a second adjusted target value by combining the second target value with the second external weight;

determining a second error based on the second target value and the second adjusted target value; and normalizing the second error value via the statistical measure; and in response to normalizing the second error value or normalizing the first error value:

generating an index value based on the first normalized error value and the second normalized error value; and transmitting, based on the index value being within a threshold percentile of a plurality of index values, an alert to one or more user computing devices.

17. The non-transitory computer-readable device of claim 16, wherein the first and second machine learning models include one or more weights corresponding to average age, percentage male, percentage female, continuously enrolled months, concurrent risk score, prospective risk score, unique acute diagnoses, chronic condition diagnoses, inpatient claimants, or member count.

18. The non-transitory computer-readable device of claim 16, wherein the index value is generated based on the average of the first normalized error value and the second normalized error value.

19. The non-transitory computer-readable device of claim 16, the operations further comprising:

in response to generating the index value, automatically generating a message including the index value, the first target, and the second target; and transmitting the message via a network to the one or more user computing devices, wherein the message comprises a link to access a graphical user interface (GUI) via the network, and wherein the link is unique to the generated index value.

20. The non-transitory computer-readable device of claim 16, wherein the statistical measure is a z-score.

* * * * *